United States Patent [19]

Yamaguchi et al.

[11] 4,380,671
[45] Apr. 19, 1983

[54] PROCESS FOR THE PREPARATION OF 2,2'-BIS(4-SUBSTITUTED PHENOL)SULFIDES

[75] Inventors: Akihiro Yamaguchi, Kamakura; Tadashi Kobayashi, Yokohama; Keizaburo Yamaguchi, Kawasaki; Hisamichi Murakami, Yokohama, all of Japan

[73] Assignee: Mitsui Toatsu Chemicals, Incorporated, Japan

[21] Appl. No.: 288,428

[22] Filed: Jul. 30, 1981

Related U.S. Application Data

[63] Continuation of Ser. No. 75,263, Sep. 13, 1979, abandoned.

[30] Foreign Application Priority Data

Sep. 14, 1978 [JP] Japan ............................ 53/112270
Aug. 2, 1979 [JP] Japan ............................ 54/98054

[51] Int. Cl.$^3$ .......................................... C07C 149/36
[52] U.S. Cl. .................................................. 568/48
[58] Field of Search .......................................... 568/48

[56] References Cited

U.S. PATENT DOCUMENTS

| | | | |
|---|---|---|---|
| 2,849,494 | 8/1958 | Cooper et al. | 568/48 |
| 2,971,940 | 2/1961 | Fuchsman et al. | 260/45.75 N |
| 2,971,968 | 2/1961 | Nicholson et al. | 260/439 |
| 3,099,639 | 7/1963 | Cobb et al. | 568/48 |
| 3,678,115 | 7/1972 | Fujisawa et al. | 568/48 |

FOREIGN PATENT DOCUMENTS

768,658 10/1967 Canada ................................ 568/48

OTHER PUBLICATIONS

G. Katsui et al., Vitamin 7, 145 (1954).

Primary Examiner—Donald G. Daus
Assistant Examiner—M. C. Eakin
Attorney, Agent, or Firm—McGlew and Tuttle

[57] ABSTRACT

Disclosed is a process for the preparation of 2,2'-bis(4-substituted phenol)sulfides which comprises reacting a 4-substituted phenol with sulfur dichloride in a hydrocarbon solvent at a temperature of from −10° to 40° C. in the presence of a Lewis acid catalyst. For example, 2,2'-bis(4-cumylphenol)-sulfide, i.e. 2,2'-bis(4-$\alpha,\alpha$-dimethyl benzyl-phenol)monosulfide, which is a novel compound can be prepared by reacting 4-cumylphenol with sulfur dichloride in benzene at a temperature of from 0° to 10° C. in the presence of zinc chloride.

14 Claims, No Drawings

PROCESS FOR THE PREPARATION OF 2,2'-BIS(4-SUBSTITUTED PHENOL)SULFIDES

This is a continuation of application Ser. No. 075,263 filed Sept. 13, 1979, now abandoned.

BACKGROUND OF THE INVENTION (1) Field of the Invention

This invention relates to an improved process for the preparation of 2,2'-bis(4-substituted phenol)sulfides which are useful as light stabilizers, polyolefin modifiers, lubricating oil additives, and intermediates for the manufacture thereof. It also relates to 2,2'-bis(4-cumylphenol)sulfide, i.e. 2,2'-bis(4-α,α-dimethyl benzylphenol)monosulfide, which is a novel compound.

(2) Description of the Prior Art

Generally, 2,2'-bis(4-substituted phenol)sulfides are prepared by reaction of a corresponding 4-substituted phenol with sulfur dichloride. However, further sulfidation in the 6-position of the resulting sulfide proceeds concurrently to form polynuclear by-products. Moreover, sulfur dichloride takes part in the chemical equilibrium represented by the equation

This leads to a more complicated reaction in which disulfides and other polysulfides are formed as by-products. In many cases, therefore, the end product is disadvantageously obtained in resinous form and in low yield.

Specifically, 2,2'-bis(4-tert-butylphenol)sulfide is conventionally prepared by reacting 4-tert-butylphenol with sulfur dichloride. For example, the reaction is effected in carbon tetrachloride at a temperature of from 20° to 30° C. However, the end product is obtained in resinous form and its identity is only approximately estimated by means of molecular weight determination (G. Katsui and H. Hisayama: Vitamin, Vol. 7, p. 145 (1954)).

Moreover, 2,2'-bis(4-tert-amylphenol)sulfide is conventionally prepared by reacting 4-tert-amylphenol with sulfur dichloride in dichloroethane. In practice, the reaction mixture is heated at reflux and then subjected to fractional distillation under reduced pressure. The resulting crude product is further purified by recrystallization to obtain an end product. However, its yield is as low as 11% (U.S. Pat. No. 2,971,940).

Furthermore, 2,2'-bis(4-methylphenol)sulfide is conventionally prepared by reacting p-cresol with sulfur dichloride in petroleum ether at room temperature. The resulting crude product is then crystallized from toluene to obtain only a 22% yield of end product (W. S. Gump and J. C. Vitucci: J. Am. Chem. Soc., Vol. 67, p. 238 (1945)).

When these prior art processes are generally applied to the preparation of 2,2'-bis(4-substituted phenol)sulfides, the reaction mixture takes a resinous form, and the resulting product not only requires a very laborious procedure for its isolation but also shows a very low yield. For such reasons, these processes cannot be regarded as economical and suitable for industrial purposes. Judging from the above-described situation of the art, it is an important technical problem to develop a process for the preparation of 2,2'-bis(4-substituted phenol)sulfides by reacting a 4-substituted phenol with sulfur dichloride in which the formation of by-products is substantially inhibited to raise the proportion of the desired product and in which the desired product can be obtained with relative ease and in good yield by subjecting the reaction mixture to common aftertreating operations.

SUMMARY OF THE INVENTION

It is an object of this invention to provide an improved process for the preparation of 2,2'-bis(4-substituted phenol)sulfides.

It is another object of this invention to provide a process for the preparation of 2,2'-bis(4-substituted phenol)sulfides in which the formation of by-products is inhibited.

It is still another object of this invention to provide a process for the preparation of 2,2'-bis(4-substituted phenol)sulfides by which the desired product can be isolated in high yield.

It is a further object of this invention to provide a process for the preparation of 2,2'-bis(4-substituted phenol)sulfides by which the desired product can be obtained with relative ease and in good yield.

It is a still further object of this invention to provide 2,2'-bis(4-cumylphenol)sulfide which is a novel compound useful as an intermediate for the manufacture of light stabilizers.

These objects can be accomplished by a process which comprises reacting a 4-substituted phenol (hereinafter referred to as the phenol reactant) of the general formula

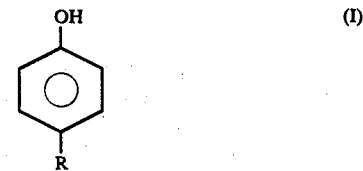

where R is an alkyl radical having from 1 to 12 carbon atoms, a cycloalkyl radical having from 3 to 12 carbon atoms, or an aralkyl radical having from 7 to 11 carbon atoms, with sulfur dichloride in a hydrocarbon solvent at a temperature of from −10° to 40° C. in the presence of a Lewis acid catalyst. In this manner, 2,2'-bis(4-substituted phenol)sulfides of the general formula

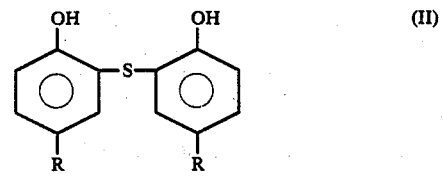

where R has the same meaning as described above, can be prepared with great industrial advantages.

In accordance with this invention, the phenol reactant is dissolved in a hydrocarbon solvent and then reacted with sulfur dichloride. However, excepting the compound of the general formula (I) in which R is tert-octyl, the phenol reactant may be totally or partially suspended in a hydrocarbon solvent and then reacted with sulfur dichloride.

In the process of this invention, a crude product can be easily isolated as a solid by, after completion of the reaction, subjecting the reaction mixture to steam distillation and thereby removing the solvent. If the product precipitates spontaneously from the reaction mixture, it can be directly isolated by filtration with great industrial advantages. In such a case, since the mother liquor from which the product has been isolated contains only very small amounts of unreacted phenol and by-products, it can be cyclically used without any adverse effect on the properties of the newly formed 2,2′-bis(4-substituted phenol)sulfide. What is more, if the product is sparingly soluble in the mother liquor, the yield of the isolated product is further enhanced by recycling the mother liquor. This not only allows a saving of solvent and hence a reduction in cost, but also substantially eliminates the problems concerning environmental pollution, thus bringing about great improvements on the prior art from an industrial point of view.

Furthermore, the process of this invention in which 4-cumylphenol is reacted with sulfur dichloride provides a novel compound identified as 2,2′-bis(4-cumylphenol)sulfide.

DETAILED DESCRIPTION OF THE PREFERRED EMBODIMENTS

The phenol reactant used in the process of this invention is a 4-substituted phenol of the general formula

(I)

where R is an alkyl radical having from 1 to 12 carbon atoms, a cycloalkyl radical having from 3 to 12 carbon atoms, or an aralkyl radical having from 7 to 11 carbon atoms. Specific examples thereof includes p-cresol, 4-ethylphenol, 4-n-propylphenol, 4-isopropylphenol, 4-n-butylphenol, 4-sec-butylphenol, 4-tert-butylphenol, 4-n-amylphenol, 4-isoamylphenol, 4-tert-amylphenol, 4-n-hexylphenol, 4-cyclohexylphenol, 4-n-heptylphenol, 4-tert-octylphenol, 4-nonylphenol, 4-dodecylphenol, 4-cumylphenol (4-α,α-dimethylbenzylphenol) and the like. Among these compounds, p-cresol, 4-ethylphenol, 4-tert-butylphenol, 4-tert-amylphenol, 4-cyclohexylphenol, 4-tert-octylphenol, 4-nonylphenol and 4-cumylphenol are preferred.

The hydrocarbon solvent used in the process of this invention can be any of the commonly used hydrocarbon solvents. Specific examples thereof include aromatic hydrocarbons such as benzene, toluene, ethylbenzene, xylene, chlorobenzene, etc.; straight-chain or branched aliphatic saturated hydrocarbons such as butane, pentane, hexane, heptane, isohexane, isoheptane, iso-octane etc.; unsubstituted or alkylsubstituted alicyclic saturated hydrocarbons such as cyclopentane, cyclohexane, methylcyclohexane etc.; and halogenated hydrocarbons such as dichloromethane, chloroform, carbon tetrachloride, dichloroethane, trichloroethane, etc. These solvents may be used in admixture. However, where the phenol reactant is 4-tert-octylphenol, aromatic hydrocarbon solvents should be used. Specific examples thereof include benzene, toluene, xylene, ethylbenzene, cumene, chlorobenzene, o-dichlorobenzene, etc. Among them, benzene, toluene and chlorobenzene are particularly preferred. These solvents may also be used in admixture. The amount of solvent used may vary widely. However, it is generally from 0.5 to 10 parts by volume and preferably from about 2 to 5 parts by volume per part by weight of the phenol reactant.

In the process of this invention, it is preferable to react every 2 moles of the phenol reactant with 1 mole of sulfur dichloride. However, the amount of sulfur dichloride used may vary from 0.8 to 1.5 moles. In effecting the reaction of the phenol reactant with sulfur dichloride, it is preferable for the purpose intended by this invention to add sulfur dichloride drop by drop to a solution of the phenol reactant in the hydrocarbon solvent. The rate of addition is preferably controlled so that the hydrogen chloride gas resulting from the reaction may be evolved continuously. If necessary, a mixture of sulfur dichloride and a hydrocarbon solvent may be added to the solution.

In the process of this invention, it is necessary to effect the reaction at a temperature of from −10° to 40° C. If the reaction temperature is lower than −10° C., the reaction time is prolonged excessively, while if it is higher than 40° C., the purity and yield of the product are reduced extremely. The preferred temperature range is from −10° to 20° C. and the most preferred temperature range is from 0° to 10° C.

The reaction of the above-defined phenol reactant with sulfur dichloride proceeds in the absence of catalyst. It is evident from the prior art, however, that the reaction rate is very slow, the reaction is so complicated as to give a resinous reaction mixture in many cases, and the purity and yield of the end product are extremely low. The process of this invention is characterized by the use of a Lewis acid as catalyst, which permits the reaction to proceed very smoothly and enhances the purity and yield of the crude product greatly. As a consequence of the use of the catalyst sulfur dichloride is consumed immediately on addition to the reaction system and, therefore, the reaction is substantially completed at the end of its addition. Specific examples of the Lewis acid include aluminum chloride, zinc chloride, stannic chloride, and ferric chloride. Among these compounds, zinc chloride is particularly preferred. The catalyst is used in a very small but catalytically effective amount which is generally from 0.001 to 0.1 mole per mole of sulfur dichloride.

In carrying out the process of this invention, a phenol reactant is either dissolved or suspended in a hydrocarbon solvent, and a Lewis acid catalyst is added thereto. While this solution or suspension is kept at a temperature of from −10° to 40° C. and preferably from −10° to 20° C., sulfur dichloride is added thereto drop by drop. After completion of the addition, the resulting reaction mixture is stirred at that temperature for a period of from 1 to 5 hours. Then, the residual hydrogen chloride gas dissolved in the solvent is expelled by blowing air through the reaction mixture.

Thereafter, the reaction mixture is worked up in one of the following two manners: (1) If the desired product is soluble in the solvent, the reaction mixture is stripped of the solvent by steam distillation and then allowed to cool to room temperature. The precipitate so formed is separated by filtration, washed with water, and dried to obtain a crude product. This crude product may be suspended in a small amount of a low-boiling aliphatic hydrocarbon, such as petroleum ether, n-hexane, etc., and then stirred at room temperature to obtain a good yield of pure product (usually having a purity of 95% or higher). (2) If the desired product precipitates as crystals from the reaction mixture, these crystals are separated by filtration, washed first with a small amount of fresh solvent and then with water, and dried to obtain an end product. As illustratively typically shown in the Examples that follow hereafter, the purity of the product is enhanced to the order of 97-98%. In either case, the resulting product may further be purified by recrystallization to obtain a highly pure product.

Where the phenol reactant used in the process of this invention is 4-tert-octylphenol, 2,2'-bis(4-tert-octylphenol)sulfide can be prepared, as described above, by dissolving 4-tert-octylphenol in an aromatic hydrocarbon (particularly, benzene, toluene or chlorobenzene) and then reacting it with sulfur dichloride at a temperature of from $-10°$ to $20°$ C. in the presence of a Lewis acid catalyst.

Among the compounds to which this invention is directed, 2,2'-bis(4-cumylphenol)sulfide, i.e. 2,2'-bis(4-α,α-dimethyl benzyl-phenol)monosulfide, of the formula

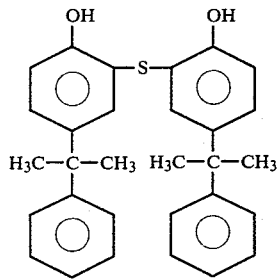

is a novel compound. This compound is obtained by reacting 4-cumylphenol with sulfur dichloride, and is useful as an intermediate or precursor for the manufacture of light stabilizers for polyolefins. For example, the nickel salts of 2,2'-bis(4-cumylphenol)sulfide imparts an equal or higher degree of light stability to polyolefins such as polypropylene, as compared with 2,2'-bis(4-tert-octylphenol)sulfide which is a well-known light stabilizer.

2,2'-bis(4-cumylphenol)sulfide can be prepared in the abovedescribed manner. For example, it can be prepared by reacting 4-cumylphenol with sulfur dichloride in benzene at a temperature of from $0°$ to $10°$ C. in the presence of zinc chloride.

The present invention is further illustrated by the following examples. The purity of the product obtained in each example was determined by high-speed liquid chromatography or gas chromatography.

EXAMPLE 1

In 90 ml of cyclohexane was dissolved 43.2 g (0.4 mole) of p-cresol, and 0.5 g of zinc chloride was added to the resulting solution. While this solution was kept at a temperature of $0°$–$10°$ C., 22.6 g (0.22 mole) of sulfur dichloride was added thereto drop by drop over a period of about 2 hours. Thereafter, the resulting reaction mixture was stirred at that temperature for 2 hours. The precipitate so formed was separated by filtration, washed first with 30 ml of cyclohexane and then with water, and dried to obtain a yield of 42.8 g (87%) of white product melting at 112°–114° C. This product was found to be 2,2'-bis(4-methylphenol)sulfide having a purity of 97.5%.

Then, the above product was recrystallized from toluene to obtain a pure product composed of white prismatic crystals melting at 116°–117° C. The results of its elemental analysis were as follows:

|  | C (%) | H (%) | S (%) |
| --- | --- | --- | --- |
| Calculated Values | 68.3 | 5.69 | 13.0 |
| Found Values | 68.5 | 5.75 | 13.4 |

EXAMPLE 2

The mother liquor and washings left behind in Example 1 were combined and a 100-ml portion was reused as a solvent. In this solvent was newly dissolved 43.2 g (0.4 mole) of p-cresol, and 0.5 g of zinc chloride was added to the resulting solution. Thereafter, the procedure of Example 1 was repeated to obtain a yield of 45.5 g (92.5%) of product melting at 112°–114° C. This product was found to be 2,2'-bis(4-methylphenol)sulfide having a purity of 97.5%.

EXAMPLE 3

In 80 ml of n-hexane were suspended 60 g (0.4 mole) of 4-tert-butylphenol and 1 g of stannic chloride. While this suspension was kept at a temperature of 5°–15° C., 22.6 g (0.22 mole) of sulfur dichloride was added thereto drop by drop over a period of about 2 hours. Thereafter, the resulting reaction mixture was stirred at that temperature for 3 hours. The precipitate so formed was separated by filtration, washed first with 30 ml of n-hexane and then with water, and dried to obtain a yield of 53.8 g (81.5%) of white product melting at 97°–98° C. This product was found to be 2,2'-bis(4-tert-butylphenol)sulfide having a purity of 98.0%.

Then, the above product was recrystallized from n-hexane to obtain a pure product composed of white prismatic crystals melting at 99°–100° C. The results of its elemental analysis were as follows:

|  | C (%) | H (%) | S (%) |
| --- | --- | --- | --- |
| Calculated Values | 72.7 | 7.87 | 9.69 |
| Found Values | 72.7 | 7.99 | 9.50 |

EXAMPLE 4

The mother liquor and washings left behind in Example 3 were combined and a 90-ml portion was reused as a solvent. In this solvent were newly suspended 60 g of 4-tert-butylphenol and 1 g of stannic chloride. Thereafter, the procedure of Example 3 was repeated to obtain a yield of 59.5 g (90%) of product melting at 97°–99° C. This product was found to be 2,2'-bis(4-tert-butylphenol)sulfide having a purity of 98.0%.

EXAMPLE 5

In 65 ml of n-hexane were suspended 32.8 g (0.2 mole) of 4-tert-amylphenol and 0.5 g of zinc chloride. While this suspension was kept at a temperature of 0°–10° C., 1.3 g (0.11 mole) of sulfur dichloride was added thereto drop by drop over a period of about 1 hour. Thereafter, the resulting reaction mixture was stirred at that temperature for 2 hours. The precipitate so formed was separated by filtration, washed first with 30 ml of n-hexane and then with water, and dried to obtain a yield of 32.0 g (89.5%) of white product melting at 98°–100° C. This product was found to be 2,2'-bis(4-tert-amylphenol)sulfide having a purity of 98.5%.

Then, the above product was recrystallized from n-hexane to obtain a pure product composed of white prismatic crystals melting at 100°–101° C. The results of its elemental analysis were as follows:

|                   | C (%) | H (%) | S (%) |
|-------------------|-------|-------|-------|
| Calculated Values | 73.7  | 8.43  | 8.94  |
| Found Values      | 73.4  | 8.61  | 8.96  |

EXAMPLE 6

In 170 ml of carbon tetrachloride were dissolved 35 g (0.2 mole) of 4-cyclohexylphenol and 0.5 g of zinc chloride. While this solution was kept at a temperature of 0°–10° C., 11.3 g (0.11 mole) of sulfur dichloride was added thereto drop by drop over a period of about 1 hour. Thereafter, the resulting reaction mixture was stirred at that temperature for 3 hours. After air was blown therethrough to expel any residual hydrogen chloride gas, the reaction mixture was stripped of carbon tetrachloride by steam distillation and then allowed to cool to room temperature. The precipitate so formed was separated by filtration, washed with water, and dried to obtain a yield of 36.8 g (theoretical yield 38 g) of crude product melting at 115°–119° C. This crude product was found to be 2,2'-bis(4-cyclohexylphenol)-sulfide having a purity of 90.0%.

Then, the above crude product was suspended in 50 ml of cyclohexane and the resulting suspension was stirred at room temperature for 10 minutes. The precipitate was separated by filtration and dried to obtain a yield of 32 g (84%) of end product melting at 121°–122° C. and having a purity of 98.5%.

This end product was recrystallized from cyclohexane to obtain a pure product composed of white needle-like crystals melting at 121°–122° C. The results of its elemental analysis were as follows:

|                   | C (%) | H (%) | S (%) |
|-------------------|-------|-------|-------|
| Calculated Values | 75.4  | 7.85  | 8.37  |
| Found Values      | 75.5  | 7.92  | 8.31  |

EXAMPLE 7

In 150 ml of benzene were dissolved 41.2 g (0.2 mole) of 4-(1,1,3,3-tetramethylbutyl)phenol and 0.5 g of zinc chloride. While this solution was kept at a temperature of 0°–10° C., 11.3 g (0.11 mole) of sulfur dichloride was added thereto drop by drop over a period of about 1.5 hours. Thereafter, the resulting reaction mixture was stirred at that temperature for 2 hours. After air was blown therethrough to expel any residual hydrogen chloride gas, the reaction mixture was stripped of benzene by steam distillation and then allowed to cool to room temperature. The precipitate so formed was separated by filtration, washed with water, and dried to obtain a yield of 43.7 g (theoretical yield 44.2 g) of crude product melting at 130°–135° C. This crude product was found to be 2,2'-bis[4-(1,1,3,3-tetramethylbutyl)phenol]sulfide having a purity of 92.5%.

Then, 43.7 g of the above crude product was suspended in 50 ml of n-hexane and the resulting suspension was stirred at room temperature for 5 minutes. The precipitate was separated by filtration and dried to obtain a yield of 39.6 g (89.5%) of end product melting at 134°–135° C. and having a purity of 98.0%. The results of its elemental analysis were as follows:

|                   | C (%) | H (%) | S (%) |
|-------------------|-------|-------|-------|
| Calculated Values | 75.97 | 9.56  | 7.24  |
| Found Values      | 76.05 | 9.63  | 7.23  |

EXAMPLE 8

The procedure of Example 7 was repeated except that the benzene was replaced by 150 ml of toluene. As a result, a yield of 43.5 g of crude product melting at 129°–135° C. and having a purity of 92.0% was obtained. Then, 43.5 g of this crude product was suspended in 50 ml of n-hexane and worked up in the same manner as described in Example 7 to obtain a yield of 39.3 g (89.0%) of end product melting at 134°–135° C. This end product was found to be 2,2'-bis[4-(1,1,3,3-tetramethylbutyl)phenol]sulfide having a purity of 98.0%.

EXAMPLE 9

The procedure of Example 7 was repeated except that the zinc chloride was replaced by stannic chloride. As a result, a yield of 43.8 g of crude product melting at 127°–131° C. and having a purity of 91.5% was obtained. Then, 43.8 g of this crude product was suspended in 50 ml of n-hexane and worked up in the same manner as described in Example 7 to obtain a yield of 39.0 g (88.2%) of end product melting at 134°–145° C. This end product was found to be 2,2'-bis[4-(1,1,3,3-tetramethylbutyl)phenol]sulfide having a purity of 98%.

EXAMPLE 10

The procedure of Example 7 was repeated except that the benzene was replaced by 150 ml of chlorobenzene. As a result, a yield of 44.0 g of crude product melting at 127°–128° C. and having a purity of 91.0% was obtained. Then, 44.0 g of this crude product was suspended in 50 ml of n-hexane and worked up in the same manner as described in Example 7 to obtain a yield of 39.2 g (88.7%) of end product melting at 134°–135° C. This end product was found to be 2,2'-bis[4-(1,1,3,3-tetramethylbutyl)phenol]sulfide having a purity of 98.0%.

EXAMPLE 11

In 150 ml of benzene were dissolved 42.4 g (0.2 mole) of 4-cumylphenol and 0.5 g of zinc chloride. While this solution was kept at a temperature of 0°–10° C., 11.3 g (0.11 mole) of sulfur dichloride was added thereto drop by drop over a period of about 1.5 hours. Thereafter, the resulting reaction mixture was stirred at that temperature for 3 hours. After air was blown therethrough to expel any residual hydrogen chloride gas, the reaction mixture was stripped of benzene by steam distillation and then allowed to cool to room temperature. The precipitate so formed was separated by filtration, washed with water, and dried to obtain a yield of 44.6 g (theoretical yield 45.4 g) of product melting at 77°–78° C. This product was found to be 2,2'-bis(4-cumylphenol)sulfide, i.e. 2,2'-bis(4-α,α-dimethyl benzylphenol)monosulfide, having a purity of 93.5%.

Then, the above product was recrystallized from n-hexane to obtain a pure product composed of white needle-like crystals melting at 82°–83° C. Its infrared spectrum as measured in the form of a KBr tablet showed absorption bands at wave numbers of 3320, 2970, 1610, 1480, 1420, 1300, 1260, 1240, 1220, 815, 790 and 710 cm$^{-1}$ and its mass spectrum had peaks at m/e values of 454, 439, 321, 212, 195, 181, 165, 119, 103, 91 and 77. The results of its elemental analysis were as follows:

|  | C (%) | H (%) | S (%) |
|---|---|---|---|
| Calculated Values (for $C_{30}H_{30}O_2S$) | 79.3 | 6.65 | 7.05 |
| Found Values | 79.5 | 6.41 | 7.07 |

What is claimed is:

1. Process for the preparation of 2,2'-bis(4-substituted phenol)sulfides of purity of the order of 93.5–98.5% and of the general formula

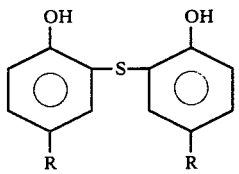

where R is an alkyl radical having from 1 to 12 carbon atoms, a cycloalkyl radical having from 3 to 12 carbon atoms, or an aralkyl radical having from 7 to 11 carbon atoms, which comprises the step of reacting a 4-substituted phenol of the general formula

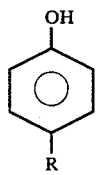

where R is the same as above, with sulfur dichloride in a molar ratio of 2 moles of phenol per 0.8–1.5 moles of sulfur dichloride in a hydrocarbon solvent or a halogenated hydrocarbon solvent at a temperature of from −10° to 40° C. and in the presence of a Lewis acid catalyst.

2. The process as claimed in claim 1 wherein said Lewis acid catalyst is selected from the group consisting of aluminum chloride, zinc chloride, stannic chloride and ferric chloride.

3. The process as claimed in claim 2 wherein said Lewis acid catalyst is zinc chloride.

4. The process as claimed in claim 1 wherein said Lewis acid catalyst is used in an amount of from 0.001 to 0.1 moles per mole of sulfur dichloride.

5. The process as claimed in claim 1 wherein said hydrocarbon solvent is selected from the group consisting of aromatic hydrocarbons, straight-chain or branched aliphatic hydrocarbons, and unsubstituted or alkyl-substituted alicyclic hydrocarbons.

6. The process as claimed in claim 1 wherein said hydrocarbon solvent or halogenated hydrocarbon solvent is used in an amount of from 0.5 to 10 parts by volume per part by weight of 4-substituted phenol.

7. The process as claimed in claim 1 wherein said reaction temperature is from −10° to 20° C.

8. The process as claimed in claim 1 wherein said 4-substituted phenol is selected from the group consisting of p-cresol, 4-tertbutylphenol, 4-tert-amylphenol, 4-cyclohexylphenol, 4-tert-octylphenol and 4-cumylphenol.

9. The process as claimed in claim 1 wherein said 4-substituted phenol is first dissolved in said hydrocarbon solvent and then reacted with said sulfur dichloride.

10. The process as claimed in claim 1, wherein said 4-substituted phenol is a 4-tert-octylphenol, said hydrocarbon solvent is an aromatic hydrocarbon and the reaction is effected at a temperature of from −10° to 20° C. in the presence of zinc chloride as Lewis acid catalyst.

11. The process according to claim 1 for the preparation of 2,2'-bis(4-cumylphenol)sulfide which comprises reacting 4-cumylphenol with sulfur dichloride in a hydrocarbon solvent at a temperature of from −10° to 40° C. in the presence of a Lewis acid catalyst.

12. The process as claimed in claim 11 wherein said Lewis acid catalyst is zinc chloride, said hydrocarbon solvent is benzene, and said reaction temperature is from 0° to 10° C.

13. The process as claimed in claim 1, wherein said halogenated hydrocarbon solvent is selected from the group consisting of chlorinated aliphatic hydrocarbons and chlorinated aromatic hydrocarbons.

14. The process as claimed in claim 1, wherein said 2,2'-bis(4-substituted phenol)sulfide resulting from said reaction precipitates as filtration-separable crystals, these crystals are separated by filtration and at least a portion of the remaining mother liquor is recycled as solvent and the step of reacting is repeated.

* * * * *